United States Patent [19]

Skipka et al.

[11] Patent Number: 4,680,146
[45] Date of Patent: Jul. 14, 1987

[54] PROCESS FOR THE PREPARATION OF 4,4'-DINITROSTILBENE-2,2'-DISULPHONIC ACID SALTS

[75] Inventors: Guido Skipka, Stolberg; Friedrich Dürholz, Remscheid, both of Fed. Rep. of Germany

[73] Assignee: Bayer Aktiengesellschaft, Leverkusen, Fed. Rep. of Germany

[21] Appl. No.: 861,486

[22] Filed: May 9, 1986

[30] Foreign Application Priority Data

May 31, 1985 [DE] Fed. Rep. of Germany ....... 3519552

[51] Int. Cl.$^4$ ............................................. C07C 143/24
[52] U.S. Cl. .................................................. 260/505 R
[58] Field of Search .................................... 260/505 R

[56] References Cited

FOREIGN PATENT DOCUMENTS

| | | | |
|---|---|---|---|
| 1159082 | 12/1983 | Canada ................................ | 260/505 |
| 0026154 | 4/1981 | European Pat. Off. . | |
| 204272 | 11/1983 | German Democratic Rep. . | |
| 57-38764 | 3/1982 | Japan . | |
| 64173 | 10/1971 | Poland . | |
| 1381730 | 1/1975 | United Kingdom . | |
| 2136430 | 9/1984 | United Kingdom ................ | 260/505 |
| 230136 | 3/1969 | U.S.S.R. . | |

OTHER PUBLICATIONS

Bender et al., *Ber.*, 19, 3234.
Fischer et al., *Ber.*, 26, 2233.

*Primary Examiner*—Alan Siegel
*Attorney, Agent, or Firm*—Sprung Horn Kramer & Woods

[57] ABSTRACT

4,4-40 -Dinitrostilbene-2,2'-disulphonic acid salts are prepared by the oxidation of 4-nitrotoluene-2-sulphonic acid or salts thereof in an aqueous alkaline medium, by adding potassium, calcium and/or magnesium ions during the reaction at the rate of which 4,4'-dinitrostilbene-2,2'-disulphonic acid is formed, the amount of added potassium, calcium and/or magnesium ions at any point during the reaction being 10 to 150 mol %, relative to the amount of 4,4'-dinitrostilbene-2,2'-disulphonic acid present in the reaction mixture at that particular time, and by removing the precipitated salt of 4,4'-dinitrostilbene-2,2'-disulphonic acid.

16 Claims, No Drawings

PROCESS FOR THE PREPARATION OF 4,4'-DINITROSTILBENE-2,2'-DISULPHONIC ACID SALTS

BACKGROUND OF THE INVENTION invention relates to a process for the preparation of 4,4'-dinitrostilbene-2,2'-disulphonic acid salts by the oxidation of 4-nitrotoluene-2-sulphonic acid or salts thereof in an aqueous alkaline medium.

The preparation of 4,4'-dinitrostilbene-2,2'-disulphonic acid or salts thereof (described as dinitrostilbene acid below) has been known for a long time and consists in subjecting 2 moles of 4-nitrotoluene-2-sulphonic acid (described as p-nitrotoluenesulphonic acid below) to an oxidative condensation reaction under aqueous alkaline conditions. Oxygen (air), in most cases in the presence of a catalyst, or sodium hypochloride or chlorine have been employed as oxidizing agents (see, for example, F. Bender and G. Schultz, .Ber., 19, 3234; O. Fischer and E. Hepp, Ber., 26, 2233; and DE-OS (German Published Specification) No. 2,258,530). Because of the poor yields of only approximately 75% in the known industrial processes, attempts have been made to increase the yields of dinitrostilbene acid by varying the reaction conditions.

Thus, in accordance with USSR Patent Specification No. 230,136, the sodium hydroxide solution is added in two stages at different concentrations (approximately 2% strength sodium hydroxide solution in the first stage and approximately 4% strength sodium hydroxide solution in the second). The yield of dinitrostilbene acid is, however, only 65% of theory at most.

East German Patent Specification No. 204,272 describes a process for the preparation of dinitrostilbene acid by the oxidation of p-nitrotoluenesulphonic acid in an aqueous alkaline medium by means of atmospheric oxygen, which is characterized in that, the higher the alkali concentration and/or the reaction temperature, the lower the concentration at which the p-nitrotoluenesulphonic acid is kept in the oxidation solution. The yields of dinitrostilbene acid are quoted as 70 to 80% of theory.

Polish Patent Specification No. 64,173 discloses a process in which the oxidation is carried out in a 4-plate column. The oxygen-air mixture is fed, at an oxygen content of 20 to 50% by volume, counter-current in a closed circuit. A concentration range from 3.1 to 10% by weight is quoted for the sodium hydroxide solution and a range from 4 to 8% by weight is quoted for the sodium salt of p-nitrotoluenesulphonic acid. The yields are 60 to 85% of theory, depending on the concentrations of the reactants.

An increase in the yield of dinitrostilbene acid to a maximum of 82% of theory is described in Japanese Patent Specification No. 8,238,764. Described as well as the catalyst are manganese sulphate, compounds of molybdenum barium. iron, nickel and cobalt or mixtures thereof.

A process for the preparation of dinitrosilbene acid and salts thereof by the oxidation of p-nitrotoluenesulphonic acid in organic solvents is described in European Offenlegungsschrift (European Published Specification) No. 26,154. Yields of up to 95% of theory are achieved in this process, depending on the mode of operation. Disadvantageous factors in this process are carrying out the reaction in organic solvents and the low reaction temperatures.

British Patent Specification No. 2,136,430 discloses a process for the preparation of dinitrosilbene acid, which is characterized in that the oxidation of p-nitrotoluenesulphonic acid is carried out in the presence of lithium and hydroxyl ions, if appropriate with the addition of a catalyst. The yields in this process are quoted as about 80 to 90% of theory. The removal of lithium carbonate before the isolation of the dinitrostilbene acid is necessary in this process as an additional stage. The recovery of lithium carbonate is only 75%, however. Additionally, the lithium carbonate removed must first be converted into lithium hydroxide before it can be re-used in the process.

As a result of the removal, which is, above all, expensive, of the lithium carbonate before the isolation of the dinitrosilbene acid, the process described in the British Patent Specification does not prove very economical.

Disadvantageous factors in the processes known hitherto for the preparation of dinitrosilbene acid are not only the yields, which, all things considered, are unsatisfactory, but also, in addition, the formation of undesirable by-products. These pollute the effluent and thereby cause considerable expense.

SUMMARY OF THE INVENTION

A process has now been found for the preparation of 4,4'-dinitrostilbene-2,2'-disulphonic acid salts by the oxidation of 4-nitrotoluene-2-sulphonic acid or salts thereof in an aqueous alkaline medium, which process is characterized in that potassium, calcium and/or magnesium ions are added during the reaction at the same rate at which the 4,4'-dinitrostilbene-2,2'-disulphonic acid is formed, the amount of added potassium, calcium and/or magnesium ions being 10 to 150 mol % at any point during the reaction, relative to the amount of 4,4'-dinitrostilbene-2,2'2,2'-disulphonic acid present in the reaction mixture at that particular time, and the precipitated salts of 4,4'-dinitrostilbene-2 2'-disulphonic acid are removed.

DETAILED DESCRIPTION OF THE INVENTION

The progress of the reaction and the formation of dinitrostilbene acid in the reaction mixture can be followed readily by means of liquid chromatography analysis (HPLC), thus enabling the metering in of the potassium, calcium and/or magnesium ions to be controlled in an optimum manner. It is advantageous to control the addition of the potassium, calcium and/or magnesium ions in such a way that, at any point during the reaction, the amount of added potassium, calcium and/or magnesium ions is 20 to 140 mol %, particularly preferentially 50 to 130 mol %, relative to the amount of 4,4'-dinitrostilbene-2,2'-disulphonic acid present in the reaction mixture at that particular time.

It is advantageous for the process according to the invention to employ the potassium, calcium and/or magnesium compounds in an ionic form, that is to say, for example, in the form of hydroxides, chlorides and/or sulphates. However, it is also possible to employ potassium, calcium and/or magnesium compounds of lower solubility, such as the corresponding oxides, in the process according to the invention.

In accordance with the invention, the oxidation of the p-nitrotoluene$ulphonic acid is carried out in an aqueous alkaline medium. Various compounds which form hydroxyl ions can be employed to prepare the aqueous alkaline medium. The only exception in this respect relates to compounds which form hydroxyl ions and form sparingly soluble salts with dinitrostilbene acid. Lithium hydroxide, sodium hydroxide and/or quaternary ammonium hydroxides can, for example, be employed in the process according to the invention. In general, the concentration of the hydroxides in the aqueous alkaline medium is about 1 to 15% by weight, preferably 2 to 10% by weight, relative to the reaction mixture.

The concentration of p-nitrotoluenesulphonic acid in the reaction mixture is usually about 2 to 30% by weight, preferably 4 to 25% by weight.

The process according to the invention is generally carried out at temperatures of about 30 to 100° C., preferably at 40° to 80° C.

The process according to the invention can be carried out either discontinuously or continuously.

The process according to the invention is generally carried out under normal pressure. However, it is also possible to carry out the process under a reduced or elevated pressure.

In an advantageous embodiment of the process according to the invention, dinitrostilbene acid is initially introduced in amounts of about 0.5 to 30 g/l, preferably 2 to 15 g/l, in the aqueous alkaline medium, the p-nitrotoluenesulphonic acid is then added, and the oxidation is then carried out, as described, with the addition of further potassium, calcium and/or magnesium ions.

Suitable oxidizing agents are pure oxygen or mixtures thereof with inert gases, such as nitrogen, especially air. It is also possible to employ other oxidizing agents, such as hypochlorides. The oxidizing agents are employed in this reaction in an excess relative to p-nitrotoluene sulphonic acid. In general, the excess of oxidizing agents used, in particular oxygen or air, is about 300% by weight, preferably 10 to 100% by weight, relative to p-nitrotoluenesulphonic acid.

In accordance with a further, advantageous embodiment, the oxidation of p-nitrotoluenesulphonic acid to dinitrostilbene acid is carried out in two stages. In accordance with this embodiment, in the first stage p-nitrotoluenesulphonic acid is oxidized, within an alkali concentration range from about 4 to 10% by weight and at temperatures of about 45° to 70° C., with an oxygen-air mixture, to give 4,4'-dinitrodibenzyl-2,2'-disulphonic acid (described below as dinitrodibenzyl acid) and a small amount of dinitrostilbene acid. The yield of dinitrodibenzyl acid and dinitrostilbene acid in this stage totals about 91%, together with about 7% of p-nitrotoluenesulphonic acid. The ratio in which these are formed depends on the temperature and the alkali concentration, and can be determined readily by analysis. Potassium, calcium and/or magnesium ions are added to the reaction mixture at the rate at which dinitrostilbene acid is formed. In the second stage, the dinitrodibenzyl acid is oxidized further to give dinitrostilbene acid. It is important in this stage to reduce to alkali concentration in the aqueous alkaline medium to about 2 to 6% by weight by dilution with water, and to raise the temperature to about 50° to 90° C. The addition of the remaining amount of potassium, calcium and/or magnesium ions is effected in this stage.

The reaction mixture is cooled for a short time and, if necessary, neutralized with dilute acid, and the precipitated salts of dinitrostilbene acid are removed in a customary manner.

The yields of dinitrostilbene acid achieved in the process according to the invention are about 90 to 7% of theory. Undesirable by-products are formed only in inconsiderable amounts, if at all. The 4,4'-dinitrostilbene-2,2'-disulphonic acid can be reduced to the corresponding 4,4'-diaminostilbene-2,2'-disulphonic acid which is a useful intermediate product for the production of dyestuffs and optical brightening agents (European Offenlegungsschrift No. 26,154).

EXAMPLE 1

125.3 g (0.31 mole) of 9.9% strength by weight sodium hydroxide solution are added to 575 g of distilled water. After the sodium hydroxide solution has been heated to 68° C., 117.1 g (0.24 mole) of 87.8% strength finely powdered dibenzyl acid are introduced. 60 l/hour of oxygen are passed into the reaction mixture. 189 g (175 ml) of 12.4% strength by weight potassium hydroxide solution (0.42 mole) are added to the reaction mixture in the course of 6 hours by metering in between 50 and 15 ml of potassium hydroxide solution per hour. After the potassium hydroxide solution has been added, the mixture is left to stand for a further 1½ hours to complete the reaction, and 30 g of potassium chloride are then introduced into the reaction mixture. The reaction mixture is neutralized by adding 30% strength by weight hydrochloric acid and is cooled overnight. 133 g of moist product, corresponding to 117 g of dry material, are obtained after the mother liquor has been removed. The yield of dinitrostilbene acid potassium salt is 94.7% of theory (according to analysis by the HPLC method).

EXAMPLE 2

1000 g of 4.5% strength by weight sodium hydroxide solution and 3 g of 4,4'-dinitrostilbene-2,2'-disulphonic acid are initially taken at 70° C. 124 g of 87.2% strength finely powdered 4,4'-dinitrodibenzyl-2,2'-disulphonic acid and 430 g of 6.19% strength by weight aqueous potassium hydroxide solution are added in small portions (approximately 20 portions) at 70° C. 50 l/hour of oxygen and 20 l/hour of air are passed into the reaction mixture for the whole duration of the experiment. After the mixture has been stirred for a further 2 hours at 70° C., a further 6 g of 100% strength by weight potassium hydroxide solution are added and the mixture is neutralized with 210 g of 30% strength by weight hydrochloric acid. 145 g of moist dipotassium 4,4'-dinitrostilbene-2,2'-disulphonate, corresponding to 124.7 g of dry material are isolated by filtration. The yield is found to be 97.2% of theory according to analysis by means of the HPLC method.

EXAMPLE 3

1000 g of 2.5% strength by weight sodium hydroxide solution are initially taken at 70° C.; 50 l/hour of oxygen and 20 l/hour of air are passed in, and 124 g of 87.2% strength by weight finely powdered 4,4'-dinitrodibenzyl-2,2'-disulphonic acid and 777 g of 3.44% strength by weight potassium hydroxide solution (divided into 20 portions) are added to the alkaline solution at and with stirring, in the course of 2 hours. The reaction mixture is left for a further 2 hours to complete the reaction, 7 g of potassium chloride are added and the mixture is neutralized with 30% strength by weight hydrochloric acid and cooled to room temperature. 148.7 g of moist dipotassium 4,4'-dinitrostilbene-2,2'-disulphonate, corresponding to 123.5 g of dry material, are obtained after filtration. The yield of 4,4′-dinitrostilbene-2,2′disulphonic acid is found to be 96.7% of theory according to analysis by means of the HPLC method.

EXAMPLE 4

The reaction is carried out continuously in a cascade consisting of four sulphonation vessels, as reactors, having a reaction volume of approximately 2.5 l of reaction volume and with continuous overflows. The reactors are equipped with a disc stirrer and a gas inlet tube. The reaction mixture which has fully reacted is collected and neutralized in a cooled stirred vessel.

50 l/hour of oxygen and 20 l/hour of air are passed into the individual reactors via a gas inlet tube for the duration of the experiment.

For start-up, reactors 1 and 2 are charged with 1 of 6% strength sodium hydroxide solution and reactors 3 and 4 are charged with 1 l of 3.5% strength sodium hydroxide solution.

The reaction temperatures in the reactors are adjusted by means of jacket heating to the following values: reactors 1 and 2 to 59° C., reactor 3 to 72° C. and reactor 4 to 70° C.

311 g/hour of 32.8% strength p-nitrotoluenesulphonic acid and 98.8 g/hour of a mixture of sodium hydroxide and potassium hydroxide solution (93.5 g of 50% strength sodium hydroxide solution and 5.3 g of 50% strength potassium hydroxide solution) are metered continuously into reactor 1.

16 g of 3.4% strength potassium hydroxide solution and 50 g of 0.002% strength manganese sulphate solution are metered continuously into reactor 3.

The reaction suspension flowing out of reactor 4 is collected in a cooled stirred vessel and is neutralized continuously with hydrochloric acid.

30 g of potassium chloride are added to the reaccipitate the 4,4′-dinitrostilbene-2,2′-disulphonic acid completely, and the mixture is stirred for a further hour.

Isolation is effected by filtration. 230 to 270 g of moist filter cake, corresponding to 185 to 220 g of dry material (approximately 83% strength in respect of 4,4′-dinitrostilbene-2,2′-disulphonic acid) are obtained. The yield of 4,4′-dinitrostilbene-2,2′-disulphonic acid was found to be 94% of theory according to analysis by means of the HPLC method and determination of the carbon content of the dried filter cake and of the mother liquor.

It will be appreciated that the instant specification and claims are set forth by way of illustration and not limitation, and that various modifications and changes may be made without departing from the spirit and scope of the present invention.

We claim:

1. A process for the preparation of 4,4′-dinitrostilbene-2,2,-disulphonic acid salts comprising oxidizing nitrotoluene-2-sulphonic acid or salts thereof in an aqueous alkaline medium, adding potassium, calcium and/or magnesium ions during the process at the same rate at which the 4,4′-dinitrostilbene-2,2′-disulphonic acid is formed, the amount of added potassium, calcium and/or magnesium ions being 10 to 150 mol % at any particular time during the process, relative to the amount of 4,4′-dinitrostilbene-2,2′-disulphonic acid present in the reaction mixture at that particular time, and removing the precipitated salt of 4,4′-dinitrostilbene-2,2′disulphonic acid.

2. A process according to claim 1, wherein the amount of added potassium, calcium and/or magnesium ions at any particular time during the process is 20 to 140 mol %, relative to the amount of 4,4′-dinitrostilbene-2,2′-disulphonic acid present in the reaction mixture at that particular time.

3. A process according to claim 1, wherein the amount of added potassium, calcium and/or magnesium ions at any point during the reaction is 50 to 130 mol %, relative to the amount of 4,4′-dinitrostilbene-2,2′-disulphonic acid present in the reaction mixture at that particular time.

4. A process according to claim 1, wherein said potassium calcium and/or magnesium ions are employed as hydroxides, chlorides and/or sulphates.

5. A process according to claim 1, wherein the process is carried out at temperatures from 30° C. to 100° C.

6. A process according to claim 1, wherein the process is carried out at a temperature of 40° C. to 80° C.

7. A process according to claim 1, wherein the 4,4′-dinitrostilbene-2,2′-disulphonic acid is initially introduced in amounts of 0.5 to 30 g/l in the aqueous alkaline medium, the 4-nitrotoluene-2-sulphonic acid is then added and potassium, calcium and/or magnesium ions are added during the oxidation reaction at the same rate at which 4,4′-dinitrostilbene acid 2,2′-disulphonic acid is formed.

8. A process according to claim 1, wherein the 4,4′-dinitrostilbene-2,2′-disulphonic acid is initially taken in amounts of 0.2 to 15 g/l in the aqueous alkaline medium, the 4-nitrotoluene-2-sulphonic acid is then added and potassium, calcium and/or magnesium ions are added during the oxidation reaction at the same rate at which 4,4′-dinitrostilbene acid 2,2′-disulphonic acid is formed.

9. A process according to claim 1, wherein said alkaline medium contains a concentration of hydroxides of 1 to 15% by weight, relative to the reaction mixture.

10. A process according to claim 1, wherein said alkaline medium contains a concentration of hydroxides of 2 to 10% by weight, relative to the reaction mixture.

11. A process according to claim 1, wherein said p-nitrotoluenesulphonic acid in the reaction mixture is 2 to 30% by weight.

12. A process according to claim 1, wherein said p-nitrotoluenesulphonic acid in the reaction mixture is 4 to 25% by weight.

13. A process according to claim 1, wherein said oxidizing is conducted with an oxidizing agent selected from the group consisting of pure oxygen, air and hypochlorides.

14. A process according to claim 1, wherein said oxidizing is conducted with an oxidizing agent, and oxidizing agent employed in an amount in excess relative to the p-nitrotoluenesulphonic acid.

15. A process according to claim 1, wherein the process is conducted in two stages, in a first stage p-nitrotoluenesulphonic acid is oxidized in an alkali concentration range from about 4 to 10% by weight and at temperatures of about 45°to 70° C., with an oxygen-air mixture to yield 4,4′-dinitrodibenzyl-2,2′-disulphonic acid and a small amount of nitrostilbene acid, potassium, calcium and/or magnesium ions being added to the reaction mixture at the rate at which dinitrostilbene acid is formed, and in a second stage the 4,4′-dinitrodibenzyl2,2′disulphonic acid being oxidized further to yield dinitrostilbene acid.

16. A process according to claim 15, wherein in said second stage, the alkali concentration in the aqueous alkaline medium is reduced to 2 to 6% by weight by dilution with water and the temperature is raised to 50° C. to 90° C., the remaining amount of potassium, calcium and/or magnesium being added to the reaction mixture at the rate at which dinitrostilbene acid is formed.

* * * * *